United States Patent [19]

Paré

[11] Patent Number: 5,458,897
[45] Date of Patent: Oct. 17, 1995

[54] MICROWAVE-ASSISTED EXTRACTION FROM MATERIALS CONTAINING ORGANIC MATTER

[75] Inventor: J. R. Jocelyn Paré, Gloucester, Canada

[73] Assignee: Her Majesty the Queen in right of Canada, as represented by the Minister of the Environment, Gloucester, Canada

[21] Appl. No.: 289,544

[22] Filed: Aug. 12, 1994

Related U.S. Application Data

[63] Continuation-in-part of Ser. No. 29,358, Mar. 10, 1993, Pat. No. 5,338,557, which is a continuation-in-part of Ser. No. 670,769, Mar. 18, 1991, abandoned, which is a continuation-in-part of Ser. No. 519,588, May 7, 1990, Pat. No. 5,002,784.

[30] Foreign Application Priority Data

May 16, 1989 [CA] Canada ................................ 600322

[51] Int. Cl.⁶ ........................................ A23L 1/00
[52] U.S. Cl. .............................. 426/241; 426/430
[58] Field of Search ............................ 426/241, 428, 426/429, 430

[56] References Cited

U.S. PATENT DOCUMENTS 4,464,402  8/1984  Gannon ................................. 426/242
4,554,132  11/1985 Collins ................................... 422/68

FOREIGN PATENT DOCUMENTS 987993   4/1976  Canada.
1209675  10/1970  United Kingdom.

OTHER PUBLICATIONS

Ganzler et al, Z. Lebensm Unters Forsch (1987) 184, pp. 274–276.
Craveiro et al, Flavor and Fragrance Journal, vol. 4, pp. 43–44 (1989).
Ganzler et al, Journal of Chromatography (1986), pp. 299–306.

*Primary Examiner*—George Yeung
*Attorney, Agent, or Firm*—McFadden, Fincham

[57] ABSTRACT

There is disclosed a method and apparatus for extraction of various substances from plant and animal and other material containing organic matter by exposure to microwave energy. The method involves exposure to microwaves of the material containing organic matter and a component which absorbs microwaves to disrupt the microstructure and to extract the substances into a suitable non-aqueous organic medium after disruption of the microstructure. The apparatus includes microwave applicators, solvent and starting material storage means and multiple stages of treatment resulting in a high quality extracted product.

20 Claims, 1 Drawing Sheet

MICROWAVE-ASSISTED EXTRACTION FROM MATERIALS CONTAINING ORGANIC MATTER

This application is a continuation-in-part of Ser. No. 08/029,358 filed Mar. 10, 1993, now U.S. Pat. No. 5,338,557, which in turn is a continuation-in-part of Ser. No. 07/670,769 filed Mar. 18, 1991, now abandoned, which is a continuation-in-part of Ser. No. 07/519,588 filed May 7, 1990 now U.S. Pat. No. 5,002,784.

BACKGROUND OF THE INVENTION

1. Field of the Invention

This invention relates to a method of extracting soluble products from materials containing or composed of biological matter or organic matter using microwave energy and apparatus therefor.

2. Description of the Prior Art

Various microwave advances have been documented where e.g. grains containing fats and oils have been dried by microwave heating, followed by steps to remove husks and to extract oils, e.g. U.S. Pat. No. 4,464,402, Gannon. Grains and seeds also have been microwave treated to heat the extracted medium, e.g. Ganzler and Salgo, 1987, Z. Lebensm Unters Forsch 184: 274–276. In these experiments, radiation was primarily employed to heat the extractant medium.

Microwave drying of food products followed by subsequent solvent extraction is disclosed in U.S. Pat. No. 4,554,132 by Collins, but with no extraction process.

British 1,209,675 discloses inactivating enzymes of palm fruits with microwave radiation, followed by solvent extraction of palm oil.

Heitkamp et al., Canadian 987,993, describes a microwave induced migration of flavour and aroma constituents towards the surface in certain tissue such as tobacco or tea in the presence of moisture and optionally a solvent. Heitkamp does not teach any enhanced extraction of the flavour or aroma constituents into the extracted medium.

Additionally, Craveiro et al. in the *Flavour and Fragrance Journal* 4, 1989: 43–44, discuss the production of volatile material from plant material exposed to microwave energy in an air stream.

Ganzler, Salgo, and Valko in *Journal of Chromatography*, 371, 1986: 299–306, disclose microwave sample preparation for organophosphate pesticides, antinutritives and crude fat samples. Dried sample materials are milled to the point of particulation and suspended in an organic medium. The Ganzler et al. method describes an extraction in which the glandular and vascular matter of the dried sample material is destroyed mechanically prior to microwave treatment; this causes a loss of volatile oils and allows for undesirable materials to be obtained. That method calls for a long centrifugation time, a well-known extraction technique. In addition, the method indicates that the suspensions of samples and solvents are cooled and subsequently re-exposed to microwaves. Thus, heating of the extraction environment occurs with no recovery of the extractant or any volatile oils.

Steam distillation and solvent extraction methods are well known in the art but are limited by high temperatures, as well as being dangerous when using certain organic solvents and being deficient in producing an uncontaminated product.

Accordingly, there is a need for an extraction method and apparatus for producing maximum yields and recovery of volatile oils and other useful substances contained in cellular biological material by microwave inducement without any of the disadvantages and inherent limitations of the prior art.

SUMMARY OF THE INVENTION

With the present invention, an extraction protocol for various natural products is provided, without being limited to, human usage, e.g. ingestion or topical application, without the hazards associated with conventional extraction techniques and which is more selective, efficient and rapid.

The present invention employs microwave energy to generate a sudden temperature increase in the glandular and sometimes vascular systems of biological material, contacted with an appropriate quantity of a suitable non-aqueous organic solvent or extractant as defined hereinafter.

According to a preferred embodiment of the present invention, there is provided a method of disrupting the microstructure of treating materials comprising organic matter having substances which are difficult to access for extraction, which comprises:
(a) providing a source of material to be treated in which the material includes organic matter having at least one component which absorbs microwave radiation;
(b) mixing the material with a solvent which is relatively transparent to microwave radiation; and
(c) exposing the resulting mixture to microwave radiation until access by the solvent to said substances is facilitated.

By "organic matter" when used herein is meant any matter containing or derived from living organisms including micro-organisms and decayed or decomposed organisms.

One aspect of the present invention provides a method of obtaining volatile oils from biological material containing such volatile oils comprising the steps of providing a source of biological material having a substantially intact glandular system, the biological material having a moisture content sufficient to permit the extraction of the volatile oils by microwave energy. In the method, the biological material is surrounded with a non-aqueous extractant for the volatile oils. Then, the biological material is exposed to a microwave energy source to effect differential heating between the biological material and the non-aqueous extractant to thereby express the volatile oils from the biological material while cooling the expressed volatile oils from the biological material with the non-aqueous extractant to a temperature below the temperature at which the expressed volatile oils are extracted from the biological material. The process may include separating residual biological material from the extracted oil in the solvent and recovering the oil.

A particularly advantageous method involves immersing a source of biological material having cellular matter containing the oils in a non-aqueous organic extractant, the source of material having a substantially intact glandular system and a moisture content sufficient to rupture the glandular system under microwave treatment. Thereafter, the source material is exposed to a microwave energy source to elevate the temperature of the biological material to a degree sufficient to rupture the glandular system and express the volatile oil from the biological material into the organic extractant.

Following recovery of the volatile oil in the organic extractant, in a first extraction step, the volatile oils extracted from the biological material are cooled with the non-aqueous organic extractant. Further, an additional source of the biological material is added to the resulting extractant, containing extracted volatile oils from the first extraction step, and exposed so that the combined biological material and the resulting extractant is treated with a microwave energy source sufficient to elevate the temperature of the biological material to rupture the glandular system of the biological material contained in the resulting extractant to express and disperse volatile oil therefrom. This may be repeated several times. In the next step, the volatile oils are separated from the further extractant thus obtained.

In accordance with a still further aspect of the present invention, there is provided a further method for extracting soluble products from material containing organic matter comprising:

(a) immersing a source material comprising organic matter and having a microstructure containing substances difficult to extract in a non-aqueous organic extractant, said source material having a moisture content sufficient to cause disruption in said microstructure under microwave treatment;

(b) exposing said source material to a microwave energy source to elevate the temperature of said material to a degree sufficient to disrupt said microstructure and release said substances from the material into said organic extractant; and (c) recovering said substances released into said organic extractant.

In a particularly advantageous embodiment, concentrated extracts of the volatile oils can be obtained upon reducing the amount of solvent normally required for that purpose. Thus, where an extractant is used repeatedly, solvent usage is reduced resulting in a more economical and valuable operation.

In contrast to other procedures, this invention causes the microwave energy to be absorbed by the material being treated in a preferential manner, compared to the solvent, so that oils expressed from the biological material are then immediately cooled by the surrounding solvent, thus avoiding exposure of the oils and sensitive materials to heat degradation by the microwave treatment of the biological material.

Therefore, compared to using a microwave absorbable solvent in prior art processes, Applicant's process is a "cool process" in which the solvent medium does not heat up due to absorption by the solvent of microwave energy and substantially all of the microwave energy used is imparted to the material being treated. The positive differential in temperature between the biological material and the extract ensures that the substance to be extracted migrates towards the extractant.

The extractant may be selected from suitable organic solvents known to those skilled in the art, for example, alkanes e.g. hexane or other such suitable non-aqueous aliphatic organics. Generally, such materials are termed "microwave transparent", i.e. they do not substantially heat-up or there is no significant microwave energy absorption upon exposure due to the lack of a molecular dipole moment. Thus, cooling of the extracted oils from cellular biological material occurs. Co-solvents may also be employed. The extractants should have a static dielectric constant of between about 0 to 28, or should be transparent to the microwave frequency of the microwave source.

In the case where the biological material is substantially devoid of any moisture, rehydration or resolvation of the material may be achieved, prior to microwave treatment, by incorporating substances which are not transparent to microwaves, i.e., those having a net dipole moment. These substances include, for example, methanol, ethanol and mixtures of solvents, saline solutions, etc.

In the event that a partially transparent organic solvent is used, the temperature of the same remains below that of the biological material and more specifically, the extracted oil, during a microwave treatment. This ensures that the oil containing matter will be cooled. It will also ensure the migration of the oil into the extractant.

Another aspect of the invention employs an extraction media system either as a single extractant or a solution of two or more suitable and compatible extractants, in series, to obtain fractionated oil extractions.

Applicant has found that by utilizing non-particulated material as the material to be treated, superior results are obtained; the prior art has proposed utilizing finely ground or particulated dried material which results in substantial non-selective alteration of glandular and vascular tissues which is, of course, a primary necessity for volatile oil extraction. By using substantially whole or large pieces of material, destruction of glandular and vascular systems is avoided resulting in higher and more valuable extraction of desired products.

Glandular tissue, as used herein, refers to those organs responsible for various secretions e.g. nectary secretions. Vascular tissue refers to channels for the conveyance of fluids. Generally, the volatile oils for extraction from biological material include the essential oils located in the glandular system. Such oils carry the essential odour or flavour of the biological material and are used in perfumes and flavourings. As is known, the volatiles, i.e. essential oils, are distinguished from the fixed oils e.g. cottonseed, linseed or coconut oils etc. in that the former oils are not glycerides of fatty acids.

As used herein, the term "volatile oils" includes not only those substances derived from plant and animal materials such as essential oils, but also substances such as lipids, fatty oils, fatty acids, etc. which, while not having the same degree of volatility as essential oils, are expressed or "volatilized" from the glandular or like system of such plant and animal materials, by the process described herein.

The present invention is applicable to a wide variety of biological materials such as various types of tissue e.g. plant material for flavouring and fragrance purposes, and other tissues e.g. animal tissue. Examples of plant material include Canadian pepper mint, seaweeds such as Irish moss, microalgaes, seeds, spices, various types of vegetables, e.g. onions, garlic, cellulosic materials and the like. In the case of animal tissue, liver, kidney, egg yolk, etc. or animal products e.g. sea anemones, sea cucumber and crustaceous products (e.g. lobster or other shell fish), warm and cold water fish (e.g. trout, etc.) can be employed to extract pigments, oils, etc. Other biological materials that may be used include bacterial cultures, cell cultures, tissue cultures, yeasts, fermentation broths, and any resulting biomass materials from such cultures e.g. callus or the like. One preferred application relates to the extraction of the desirable oils from fish components such as the liver which are a source of desirable acids for pharmaceutical and human purposes e.g. volatile oils such as omega-3 and omega-6 oils and the like and the resulting biomasses therefrom. Other biological materials include soils containing one or more extractable materials in which the extractable material is capable of absorbing microwave energy in a transparent or semi-transparent solvent; such soils as containing plant material, or even plant material per se, as well as microalgae, can also be advantageously used in the present invention. In the case of the biological material being a source of microalgae, various types of materials can be extracted from the microalgae, such as fatty acids, different types of health foods, pigments and the like, the latter being useful for e.g. the cosmetic industry. In the case of the biological material being a plant material, various types of components can be extracted depending on the particular type of plant material such as fatty acids from numerous plants, glycerides, etc. (e.g. from canola, olive, peanut, cotton and linseed plants).

Still other biological materials that can be used in the process of the present invention include processed foods, such as cakes of various types. Still further organic or biological materials include various types of petrochemical sources, which can be treated to provide extracted components such as $C_{30}$ to $C_{40}$ waxes, etc. In still further embodiments, other sources of biological materials or organic matter include the deposits known as low grade coals and peats, or even biomasses such as corals.

The present invention also provides an apparatus for the extraction of essences and other substances from biological material, comprising at least one microwave applicator and includes means for feeding a mixture of biological material and an extractant through the microwave applicator for treatment. Further, means are provided for separating liquid from the treated mixture and removing the extractant from the filtered liquid.

The microwave applicator may operate within available known parameters e.g. a power rating of about 50–200 Watts at the lower end to 10,000 Watts or even significantly higher and a frequency range known to those skilled in the art. Without being limiting, such frequency range can be, for example, within about 2,000 or lower to about 30,000 MHz or higher. Any wavelength within the microwave spectrum which is absorbed to some extent by a component of the material, can be used as only minor changes in the irradiation time are necessary to compensate for changes in absorption. Several such apparatus applicators may be provided in parallel for exposure of the biological material thereby.

The apparatus provides a solvent reservoir of suitable material compatible with the organic solvents, and solvent inlet and sample inlet means. The mixture is fed into or through the applicator by a suitable means e.g. a pump and is subsequently passed into the filtering means e.g. filter paper stages, Teflon (TM) screening etc. for removal of residual plant material. In addition, the apparatus may include means for removing any water content derived from samples being treated; such means may include, e.g. suitable desiccants for this purpose which may be incorporated as a separate stage or into, e.g. the filtering means.

The material is preferably pumped to a separator e.g. a rotary vaporizer etc. for separation of the solvent from the oil material. The solvent may, additionally, be passed through a condenser such as those known in the art, for condensing the solvent.

Those skilled in the art will appreciate that the "passing" of the material mentioned herein is achieved through the use of suitable connecting lines e.g. glass tubing, Teflon (TM), quartz or other microwave transparent equipment for microwave treatment. In addition, the lines include suitable valves, e.g. glass or Teflon stopcocks etc.

BRIEF DESCRIPTION OF THE DRAWING

Having thus generally described the invention, reference will now be made to the accompanying drawing, illustrating a preferred embodiment.

With respect to the method, the microwave irradiation process generally proceeds as follows: the microwave rays travel freely through the microwave-transparent extraction medium and are allowed to reach the inner glandular and vascular systems of the biological material [a microwave transparent medium can be defined as a medium that does not possess a significant static dielectric constant i.e. net dipole moments, e.g. hexane (1.9), carbon tetrachloride (2.2), and liquid $CO_2$ (1.6 at 0° C. and 50 atm.) as opposed to large dielectric constant substances, e.g. water (80.4)]. A subdivided portion of these microwave rays is absorbed by the biological material; the absorption efficiency is largely related to the moisture content (or added absorbing component) of the material at the time the extraction process is carried out. The result is a sudden rise in temperature inside the material which is more pronounced in the glandular and the vascular system. The temperature keeps rising until the internal pressure exceeds the capacity of expansion of the cell walls thus creating an explosion at the cell level. Substances located in the cells are free to flow out of the cells migrating to the surrounding medium that is cool and traps and dissolves the oils. The solid biological material can be removed, e.g. filtered-off with the resulting solution being processed in the same manner as any other natural product extract.

The extractant amount used to contact or submerse the feed material can vary widely, normally sufficient to extract substantially all of the desired components to totally physically cover the biological material. The ratio of extractant to feed material (L/kg) can be e.g. about 1:1 to about 20:1.

Electron micrograph examination of freshly extracted plant material reveals that the degree of disruption in the internal structure of the gland system of, e.g. Canadian pepper mint, is as large for a 20-second microwave-induced extraction as it is for conventional 2-hour steam distillation and for 6-hour Soxhlet extraction processes. Electron micrographs also provide an explanation for the superior quality of the extracts obtained as the relatively short period of extraction e.g. 2 to 3 minutes can be varied so that the penetration power based on the extraction medium can be controlled. In the case of an essential oil from pepper mint, using e.g. hexane as solvent, the short extraction period combined with the use of non-particulated fresh material prevents pigments and other undesirable components that are located within the plant to be accessed by the extractant. Macerated material is used in conventional steam distillation and other extraction processes where the final mesh size is very critical, and implies an extra step, compared to this invention. Direct visual examination corroborates this phenomenon as extracts obtained by this invention are far less pigmented than steam distillation counterparts.

This invention permits the possibility of using a system of extraction media, whether as a single extractant or a solution of two or more extractants, also in series, in order to obtain fractionated extracts in a matter of minutes and making use of the same equipment. Current technology requires separate distillation processes that are costly and time consuming. Different and extensive instrumentation is also required, resulting in a much larger capital investment. This invention enables a producer to perform a series of extraction and fractionation processes at the same site, using the same equipment, in less time than is required by current technology.

The period of time necessary to irradiate the material to extract the oils with microwave rays varies with the variety of the plant or other biological material; typical times being from about 10 to 100 seconds. Irradiation times also vary with the moisture content of the feed material since water is very efficient at absorbing microwave rays. The moisture content of the material should be from about 25% to about 90%. This extraction method can be used for batch processes as well as for continuous processes.

The extraction product may be recovered from the extractant (after separation from the residual solid plant material as by screening, filtering or centrifuging) if desired by distillation, reverse osmosis, preferential extraction, chromatography, etc. Suitable recovery techniques are known to those skilled in the art. The depleted extractant phase may be recycled without further purification.

Reference will now be made to the examples of the invention provided below wherein microwave radiation-induced extraction was used. Disruption of the glandular and vascular systems of a variety of materials, as in the particular manner described herein, demonstrate the improvements. These include, for example, yield, quality of the extract, reduced time and production costs (reduced personnel costs and reduced operational costs), reduced raw material costs (because of reduced raw material preparation costs), reduced number of operations, and reduced process-related hazards (to humans and to facilities), or a combination thereof, over the conventional extraction processes. These examples are illustrative and typical, but not exhaustive or limiting.

EXAMPLE 1

For comparative purposes, the essential oil of pepper mint (*Mentha piperita*) was obtained by a 2 hr. steam distillation in yields of about 0.3% based on finely ground, freshly harvested plant tissue (two particular steam distillation experiments gave yields of 0.264% and 0.290%).

For the purpose of this invention, freshly harvested mint plant tissue was formed into non-particulated pieces about 1 cm in size thus leaving most of the glandular cells intact. Three 100 g samples were each placed into open vessels into which 250 ml of microwave-transparent hexane at room temperature was poured thereby immersing the material. These samples were subjected to microwave exposure to establish differential heating between the microwave-transparent hexane and the glandular cells of the mint plant tissue. The period of exposure was 40 seconds applied at 625 Watts and at a frequency of 2450 MHz. The glandular cells, as a result of the exposure, ruptured and dispersed the oils contained therein into the hexane for cooling. The residual mint tissue was then removed on a coarse filter paper and the mint oil extracted into the hexane was subsequently recovered from the hexane by evaporation in vacuum. The mint plant material produced an oil at comparable yields to steam distillation for 2 hrs. Three microwave extraction experiments resulted in yields of 0.474%, 0.343% and 0.296%; the yields being dependent upon the residual moisture content of the feed material which, in this case, was 80% by weight.

The quality of the microwave extracts obtained by example was superior to the steam distillation extract, as evidenced by the lower percentage of pulegone and higher percentages of menthol and menthone; a sales revenue weighted factor was used to demonstrate (Table I) the economic advantages of this invention. While the microwave-extracted oil was of a higher grade (and higher market value) this was ignored in the cost comparison in Table I, where it is evident that the net revenue factor (or difference between cost and expected sales revenue) was almost twice that of conventional steam distillation. In other words, Table I shows that the use of this invention would lead, in this particular case, to a net profit 94% greater than the results of the current steam distillation process.

TABLE I

| Factor | Conventional Steam Distillation | Microwave Process |
| --- | --- | --- |
| Revenues from sales | 1.00 | 1.00 |
| Purchasing of raw materials | 0.46 | 0.46 |
| Processing costs | 0.24 | 0.13 |
| Manpower costs | 0.11 | 0.055 |
| Containers and labelling | 0.0075 | 0.0075 |
| Net revenue factor | 0.18 | 0.35 |

EXAMPLE 2

Example 2 presents specific data of another plant material, with respect to the changed nature of the extract contents, compared to steam distillation extracts.

Sea parsley, having a 90% moisture content, obtained in Canada, was cut into pieces about 2.5 cm so that the glandular system was substantially intact. Samples of 100 g of similarly chopped material having an 80% moisture content were immersed in 250 ml hexane and subjected to microwave energy (power 625 watts, frequency 2450 MHz) for 40, 50 or 60 seconds.

Comparative samples of the chopped material (90% moisture) were subjected to steam distillation for 90 min. The percentage of oil steam distilled or extracted into hexane was then calculated. Apiole, an important constituent, was determined in the feed and in the extracted oil by gas chromatography. Results are given in Table II.

The market value of sea parsley essential oil is highly dependent upon apiole content. Table II shows the superior contents of apiole in the essential oil obtained by this invention compared to steam distillation.

TABLE II

| Process | % apiole in feed | % oil extracted | % apiole in oil |
| --- | --- | --- | --- |
| Steam distillation (90 min; 1" pieces) | 0.151 | 0.225 | 67.1 |
| Steam distillation (90 min; macerated) | 0.139 | 0.210 | 66.3 |
| Microwave irradiation (40 s; in hexane) | 0.130 | 0.165 | 78.3 |
| Microwave irradiation (50 s; in hexane) | 0.136 | 0.180 | 75.6 |
| Microwave irradiation (60 s; in hexane) | 0.121 | 0.161 | 75.2 |

Table II also shows that use of this invention led to a somewhat smaller (by 25%) essential oil extract size, but the quality of which, as determined by its apiole contents, was greater (by 15%). Furthermore, the microwave extraction results of Table II were carried out with sea parsley containing only 80% of residual moisture, whereas the steam distillation experiments were performed with material containing 90% residual moisture content. The material for microwave extraction was less costly to acquire because of its reduced cost (sold on a per weight basis) and its reduced apiole contents (as water evaporated off it carried apiole with it). It is noteworthy that the microwave extraction process not only provided a better apiole extraction yield, but it did so with plant material that had a reduced apiole starting content. This clearly shows the net "value added" obtained when employing this invention. The result is that a relatively larger net revenue (due to the combination of the two factors, namely reduced raw material supply cost and higher priced extract, exceeding the reduced production factor) is obtained by the present invention.

EXAMPLE 3

Steam distillation of cedar (*Thuja occidentalis*) produces an essential oil that suffers from its elevated content of less volatile components. To remedy this, it is necessary to shorten the extraction process time or to proceed with a subsequent fractionated distillation process. The former implies costly reduced yields whereas the latter is indicative of higher production costs and a more than doubled production time. This invention can be used to alleviate these problems in a manner whereby two fractions can be obtained, in an overall production time that is still less than the time required to proceed to single steam distillation product. Furthermore, the light or hexane fraction obtained by this two-stage extraction had a higher market value compared to the steam distillation extract since it was cleaner in terms of having less of heavy, undesired components.

Table III depicts these features from tests where fresh cedar material was subjected to a 2 hr. conventional steam distillation process in one experiment; or to two 30 sec microwave irradiation treatments, in series, on the same material, one treatment while immersed in ethanol and the other while immersed in hexane. The data in Table III are normalized with respect to the ten most important constituents of a steam distilled essential oil sample taken as determined from a gas chromatographic separation procedure (on a fused silica column of type DB-5 with appropriate temperature programmation). This GC procedure is the usual means of evaluating the contents of a given essential oil. The power of the second microwave treatment was reduced to 312.5 watts (from 625 watts) for hexane extraction to further reduce the processing costs and to take into account that the vascular system of the plant material had already been disrupted in the first microwave treatment. It has been found in other tests that proceeding to a steam distillation on material that had already been subjected to microwave irradiation, while immersed in ethanol, led to an extract of similar contents to that of the hexane extract described in Table III, i.e. devoid of its heavy fraction contents.

because of its greater cleanliness, i.e. lack of contaminants, when compared to conventional steam distillation products, since the hexane extract was devoid of undesired heavier fractions removed in the ethanolic extracts. The microwave-induced ethanolic extract, obtained in this first microwave treatment, can be used in the same manner as fractions that are obtained by more tedious, costly fractionated distillation processes, e.g. "as is" in oleoresin formulations. As in the previous examples, both ethanol and hexane in these microwave extractions remained cool with respect to the plant material due to the differential heating, thus expressing a high content of oil into the hexane and ethanol. A further advantageous consequence of this is that the main fire and explosion hazards and the special ventilation requirements concomitant with conventional extraction techniques employing inflammable and/or volatile solvents, are substantially reduced.

EXAMPLE 4

It is well recognized that some natural product extracts are highly sensitive to heat treatment because of the high lability of its contents. Garlic suffers heavily from this phenomenon which represents a major hurdle to the production of an extract of reproducible quality that can satisfy the consumers' demand for uniformity. It has been shown in the literature that a large fraction of garlic extracts known to date consist of artefacts produced during the heat-derived extraction scheme. Steam distillation, although considered a relatively mild heat treatment, suffers from the same pitfalls, i.e. leads to similar artefacts being produced. Throughout the microwave-induced extraction of this example, the garlic system remained close to ambient temperature.

Garlic, having a 30% moisture content, was chopped to a size of about 1 cm and 100 g samples were immersed in 250 ml of dichloromethane. Samples of the chopped material were subjected to steam distillation for 2 hrs. Samples in dichloromethane were subjected to microwave (625 watts, 2450 MHz) for 30 seconds and similar to the previous examples, the dichloromethane was cool with respect to the garlic sample. The oil extract was recovered by vacuum evaporation and analyzed for its components by gas chromatography.

Table IV shows that the contents of the microwave-

TABLE III

| Extraction Conditions | 10 Most Important Components of Cedar Essential Oils (%) | | | | | | | | | |
|---|---|---|---|---|---|---|---|---|---|---|
| | 1 | 2 | 3 | 4 | 5 | 6 | 7 | 8 | 9 | 10 |
| Steam distillation | 2.02 | 15.9 | 61.3 | 10.9 | 3.05 | 1.86 | 1.93 | 0.92 | 0.97 | 1.26 |
| Microwave: | | | | | | | | | | |
| Ethanolic extract | 0 | 0 | 3.15 | 0 | 0 | 0 | 0 | 0 | 39.6 | 54.3 |
| Hexane extract | 2.63 | 14.1 | 59.7 | 11.1 | 3.68 | 0 | 5.03 | 3.85 | 0 | 0 |

A sequential use of microwave treatments with a combination of solvents or solvent systems yields, in this particular example, a higher market value essential oil (hexane extract)

induced extract possessed two unreported sulphur-containing compounds B and C. The relative yields obtained for these two compounds were very reproducible from one experiment to another.

TABLE IV

Composition of Garlic Extracts (%)

| Microwave Irradiation (30 sec; in CH₂Cl₂) | | | Steam Distillation (2 hr) | | | | | | | |
|---|---|---|---|---|---|---|---|---|---|---|
| A* | B | C | A* | D | E | F | G | H | I | J |
| 22.2 | 28.4 | 49.4 | 14.7 | 5.80 | 45.9 | 9.92 | 8.96 | 4.84 | 5.96 | 3.94 |

*Component A is the only component that is common to both extracts.

Results typified by Table IV, show that the use of this invention led to a stable garlic extract consisting primarily of natural products B and C, that are not process related artefacts since they were reproducible and not altered by changed conditions (as is the case for garlic extracts obtained from conventional extraction procedures). The ratio of components B/C of the microwave irradiated extracts was reproducible within 0.5% in repeated tests. Component A, that is also found in steam distillation extracts varied more; thus it might be a process related artefact as well. All components in the steam distillation extracts varied widely (over 10%) between samples that were produced at the same time and with the same extraction conditions. It is apparent from the data that the process according to the present invention leads, in some cases, to the development of novel more reproducible ingredients for the food, feed and pharmaceutical industries, that were not extractable with any previously known extraction procedures.

EXAMPLE 5

*Monarda fistulosa*, a novel species of Monarda is a new product for perfumery and flavouring starting materials. It produces much higher concentration of geraniol in its essential oil than other genera within the Monarda. For comparative purposes, the essential oil of *Monarda fistulosa* was obtained by this method. In this example, 30 g of the fresh plant material were torn into fairly large pieces (same lot as for steam distillation) and placed in a 400 mL beaker and immersed in 175 mL of hexane and the temperature of the mixture was recorded; the mixture was submitted to a 15-second microwave irradiation period (of 500 W and at 2450 MHz) and the temperature of the medium was again recorded; this last step was repeated twice with taking further temperature measurements (i.e. a total of 45 seconds of microwave irradiation was applied and a total of 4 temperature measurements were taken). The data indicate that the internal temperature of the plant material became elevated during the exposure to thereby establish the required temperature gradient necessary for high extraction efficiency of the oils, etc. into the cooler hexane medium, (temperatures of only 15, 29, 44 and 57° C. were reached by passive heat conduction from the plant material for microwave exposure period of 0, 15, 30 and 45 seconds, respectively). The yield was found to be 1.49%.

The cellular temperature of the plant material is high, i.e. of the order of 100° C. owing to moisture content, and the intracellular moisture diffuses into the hexane medium to cause a slight temperature change, however this temperature is low in comparison to the oil material and therefore did not affect the temperature gradient to any appreciable extent evident from the extraction data.

Subsequent to the mixture of the oils and extractant medium cooling, the mixture was then filtered over a small quantity of sodium sulphate (to remove traces of water) and washed with 50 mL of fresh hexane. The extract was reduced, the yield was determined and the extract was analyzed by gas chromatography coupled to a mass selective detector (the mass spectral data being compared to a library of standards). The data are summarized in Table V.

The same microwave-assisted experiment was repeated as per above until the last filtration step. At that point, instead of reducing the extract, the extract is used as an extraction medium to perform two other sets of experiments, i.e. a total of 90 g of plant material is extracted (in three lots of 30 g, each being submitted to three irradiation sequences of 15 seconds) in a single aliquot of hexane. The total extraction was then filtered (over a small quantity of sodium sulphate), rinsed with another 50 mL of fresh hexane and reduced. The yield was determined and the contents were analyzed under the same conditions as per above. The yield (1.54%) and the sample contents proved to be identical to those noted above within the experimental error. Table V summarizes the analytical results and shows that, again, the microwave-assisted extract was of greater commercial market value by virtue of its enhanced contents in geraniol.

TABLE V

| | Relative Concentration | |
|---|---|---|
| Component | Microwave process | Steam Distillation |
| Octen-3-ol | 0.23 | 0.28 |
| Myrcene | — | 0.59 |
| p-Cymene | — | 0.12 |
| α-Terpinene | 0.21 | 0.96 |
| Linalool | 0.37 | 0.62 |
| Nerol | 0.57 | 0.33 |
| Geraniol | 98.48 | 94.83 |
| Germacreen D | 0.14 | 1.47 |
| Total | 100.00 | 99.20 |

A cumulative and sequential use of microwave-assisted extractions, combined to a judicious use of an appropriate solvent provides an extract in greater yield (1.5%) than conventional steam distillation products (0.94%) alone. Also, the extract is of higher commercial market value and reduces the quantity of solvent, another desirable factor. Furthermore, the time required to reduce and/or evaporate the extract to dryness is reduced to one-third. The latter enhances the efficiency of the process and reduces costs associated with manpower and energy consumption; in fact, reduction and/or evaporation of the solvent is the rate-determining step of this microwave-assisted extraction process. In the above example, three complete extracts are produced within ten minutes, whereas the same extract would have required a minimum of eight hours by conventional steam distillation processes.

EXAMPLE 6

Intact garlic cloves having a 30% moisture content were immersed in 250 mL of dichloromethane. The immersed samples were then irradiated with microwave radiation at 625 Watts and a frequency 2,450 MHz for a single 30-second exposure period. The samples, being completely intact in this example, illustrated exemplary constituent extraction with no contamination of the extracted constituents with less desirable constituents. Yields were found were to 22.2% for diallyl sulfide, 28.4% for 3-vinyl-1,2 dithi-5-ene and 49.4% for 2-vinyl-1,3 dithi-4-ene. The analysis of the products produced by the process herein is identified as $\mu$-wave$_2$.

TABLE VI

GARLIC CONSTITUENTS

| Constituent | HD$_1$ | HD$_2$ | CO$_2$ | $\mu$-wave$_1$ | $\mu$-wave$_2$ |
|---|---|---|---|---|---|
| Allyl methyl sulfide | — | — | — | 1,23 | — |
| Dimethyl sulfide | — | — | 1.41 | — | — |
| Diallyl sulfide | 1.33 | 3.89 | — | — | — |
| Allyl methyl disulfide | 3.05 | 5.32 | 5.58 | 8.12 | — |
| Methyl prop-1-enyl disulfide | — | — | — | 5.41 | — |
| Methyl prop-2-enyl disulfide | — | 1.26 | — | — | — |
| Dimethyl tri-sulfide | — | — | — | 1.12 | — |
| Diallyl disulfide | 31.2 | 30.7 | 16.7 | 17.7 | 22.2 |
| Dipropenyl di-sulfide | 1.38 | 1.83 | — | — | — |
| Diprop-2-enyl di-sulfide | 4.76 | 6.88 | 1.41 | — | — |
| Allyl methyl tri-sulfide | 11.2 | 12.4 | — | 7.38 | — |
| 3-vinyl-1,2-dithi-5-ene | — | — | 23.3 | 4.47 | 28.4 |
| 2-vinyl-1,3-dithi-4-ene | 1.84 | — | 46.5 | 34.3 | 49.4 |
| Diallyl trisulfide | 33.8 | 22.4 | — | — | — |
| Dipropenyl tri-sulfide | — | — | — | 2.29 | — |
| Diallyl tetra-sulfide | 1.04 | — | — | — | — |
| Dipropenyl tetra-sulfide | 4.24 | 1.32 | — | — | — |

HD$_1$ denotes hydrodiffusion; HD$_2$ denotes hydrodistillation; CO$_2$ denotes supercritical fluid extraction with CO$_2$; $\mu$-wave$_1$ denotes macerated garlic in dichloromethane with 4 irradiations of 125 seconds; $\mu$-wave$_2$ denotes intact garlic cloves in dichloromethane and irradiated for a single 30-second microwave irradiation period.

The data clearly illustrate that even under brief exposure time (30 seconds) coupled with a cool medium for the extraction of the constituents, the technique of the present invention greatly exceeds the conventional techniques of hydrodiffusion, hydrodistillation, supercritical fluid extraction and, more importantly, microwave extraction where the sample was macerated and over exposed to microwave energy.

EXAMPLE 7

A fresh rainbow trout (*Salmo galrdneri*) was provided and the pectoral fins, together with the dorsal fin and the head, were removed to form a source material for a first extraction (38.5 g). From the same fish, the complete internal parts were separated to provide a source material for a second extraction (34.9 g).

Each of these source materials were then subjected to a sequential series of microwave extractions (3×15 seconds) using the same extractant, according to the present invention. The apparatus employed was that described in Example 1; the extractant employed for each source material was hexane (a single 60 ml aliquot) which immersed the materials completely. It is important to note that the source materials were in a non-particulated state. In addition, the temperature of the extractant remained at a point where the extractant functioned to cool the expressed oil from these source materials.

The oils expressed from the starting materials were then separated from the hexane by procedures described in the other examples and the recovered products were analyzed for their fatty acid contents.

As reported in the Agricultural Handbook 8–15 (U.S. Department of Agriculture, 1987), pressing of rainbow trout to separate fatty acids from edible parts yields, by conventional techniques, a total of about 3.4% of free fatty acids. In general terms, such pressing techniques require a significant amount of time, which by comparison to the techniques of the present invention, represent several times that of the microwave extraction technique herein. In addition, the percentage yield using the process of the present invention, for the fatty acids, and using only trout fins and a small content of flesh as source material, is somewhat larger (3.9%) to the yields by conventional techniques when using whole edible fish parts. Furthermore, using the fish internal parts with the present invention, approximately five-fold (16.1 vs. 3.4%) increase in the amount of fatty acids was obtained compared to the conventional pressing techniques.

Other examples showing different biological materials follow, showing the wide application of the invention to numerous types of materials.

EXAMPLE 8

As an example describing a biological material possessing a well-defined microstructure that differs from glands and vessels, a sample of coarsely crushed (e.g. 0.1 to 1 cm) dried paprika (30 G) from Morocco was placed in an erlenmeyer and immersed with hexane (200 mL). The mixture was subjected to microwave irradiation operating at 2450 MHz and at a nominal power of 625 Watts for 30 seconds. The resulting dark red solution was filtered over anhydrous sodium sulphate and the remaining vegetable biomass was rinsed with hexane (2× 30 mL). The extract was evaporated in vacuo and subsequently analyzed by thin layer chromatography as well as for its appearance, colouring properties and for its behaviour on salt plates.

For comparison purposes, a sample of biological material issued from the same lot was extracted using the standard reference extraction method using dichloromethane as a solvent (ASTA No. 20.1). This extraction was performed the same day as the extraction using this invention and the resulting extract was subjected to similar analyses. A sample of an extract produced and provided by the grower, prior to shipment to Canada, was also subjected to similar analyses. Finally, one commercial oleoresin sample, marketed as "100,000 international units of colour (IUC)" was purchased and also submitted to similar analyses.

All analyses methods along with the standard reference extraction method will be well known to those skilled in the art.

The extract produced by this invention was somewhat darker and offered a slightly deeper red colour than the commercial product (more orange than red) and deeper colour than the standard extract produced from fresh material (more brownish hues). It also offered a much deeper and much more intense colour than the extract obtained by the standard reference method performed at the same time as this invention. The viscosity of the extract produced by this invention was less than that of the commercial product, although it was more viscous than the standard extract.

The absolute values of IUC were measured and rated as follows: extract from this invention, 140740 IUC; extract obtained by standard procedure from fresh material, 30, 595 IUC; extract obtained by standard procedure from dry material 7, 640 IUC; commercial oleoresin 108,684 IUC.

The extracts were also tested for their behaviour on salt plates and similar results were found. For example, when diluted to a same IUC level (i.e. 22% of extract produced by this invention in salad oil versus 28% of the commercial oleoresin in salad oil versus the extract obtained from fresh material and used as is) and deposited on a 2% extract, 2% polysorbate 80 and 96% sodium chloride plate, the extract produced by this invention gave superior colour results than those obtained for the commercial oleoresin, which in turn gave superior colour results than the extract obtained from fresh material.

These same plates were used to determine the stability of the extracts to light exposure, The extract produced by this invention proved to be much more stable than the others, namely 35% of IUC left after 3 days, whereas the best of the other samples, after the same exposure time to light, offered only 20% of IUC left.

Finally, solubility tests were performed. All three extracts offered similar solubility characteristics when applied to an oil surface. All three extracts offered closely similar solubility characteristics when applied to a water surface.

In summary, the use of this invention, in this particular example, led to a product that was much superior in terms of colour characteristics, that offered better fluidity and enhanced handling characteristics, was more stable to weathering such as exposure to light, and offered similar dispersion and solubility characteristics. All of these assets make for a greater value-added product. Furthermore, the use of hexane over dichloromethane will be appreciated by those skilled in the art because of its greater ability in food processing and its reduced purported health hazards.

The thin layer chromatography analysis also indicated that the extract obtained by the use of this invention contained more trace level substances that need to be further characterized in view of their potential pharmaceutical, nutritional, or medicinal properties. The use of this invention, in this particular example, made the extraction of these substances possible where other techniques failed.

EXAMPLE 9

In their original form, celery seeds, a praised aromatic and flavouring substance with numerous food applications, are made of well-defined microstructural characteristics, as it is the case for basically any vegetable material. As an example describing a biological material that has been previously processed, in this example ground to a powdery state, but that still possesses a well-defined residual microstructure, a sample of food-quality celery seeds powder (20 G) was placed in an erlenmeyer and immersed with hexane (50 mL). The mixture was subjected to microwave radiation operating at 2450 MHz and at a nominal power of 620 Watts for 30 seconds. The resulting solution was filtered over anhydrous sodium sulphate and the remaining vegetable biomass was rinsed with hexane 3×20 mL). The extract was evaporated in vacuo and subsequently analyzed by gas chromatography-mass spectrometry as well as for its organoleptic properties. This extract is hereafter referred to as MAP-9-1.

Another sample of celery seeds powder (20 G) was placed in an erlenmeyer and immersed with ethanol (50 mL). The mixture was subjected to a sequential microwave irradiation operating at 240 MHz and at a nominal power of 625 Watts that consisted of a 10-second irradiation period, a 30-second standing period and another 10-second irradiation period (i.e. a total of 50 seconds with 20 seconds of irradiation). The resulting solution was filtered over anhydrous sodium sulphate and the remaining vegetable biomass was rinsed with hexane (3×20 mL). The extract was evaporated in vacuo and subsequently analyzed by gas chromatography-mass spectrometry as well as for its organoleptic properties. This extract is hereafter referred to as MAP-9-2.

A sample of an extract certified to have been produced from the same lot of vegetable material was obtained from the same manufacturer. For comparison purposes, it was also subjected to similar analyses.

All analyses methods along with the standard reference extraction method will be well-known to those skilled in the art.

The commercial product is a slightly viscous, lightly brownish-green liquid with a distinctive celery aroma. The extract MAP-9-1 possessed a weak celery aroma and was a two-phase mixture made up of a medium-coloured brownish-green liquid and a thick, viscous, deep brownish-green layer. The extract MAP-9-2 was a deep brownish-green liquid that possessed a medium celery aroma and a viscosity somewhat grater than the commercial product.

When applied onto salt plates (2% extract, 3% polysorbate 80, and 95% sodium chloride) the organoleptic properties were determined as follows. The commercial product presented an oily aspect and was characterized by a light yellowish-green hue; it possessed a strong and distinctive celery aroma as well as a characteristic, strong and bitter celery flavour. The extract MAP-9-1 was also oily but exhibited somewhat less colour and aroma. The extract MAP-9-2 was identical in all aspects to the commercial product.

The samples were diluted at 1% in 99% water and further tested. The commercial product led to a cloudy solution with a very weak yellow-green hue that possessed a full, very bitter, celery flavour. The extract MAP-9-1 led to a clear greenish-yellow solution that possessed a slightly bitter, moderate celery flavour. The extract MAP-9-2 led a solution that was identical to that obtained from the commercial product.

The solubility of the samples was determined in oil and in water. The commercial product was entirely soluble in oil without stirring, but totally insoluble in water. The extract MAP-9-1 was partially soluble in oil when stirred; in water it is partially soluble as it added a yellow-green hue to the water although insoluble particles were still visible. The extract MAP-9-2 exhibited solubility properties that were identical to those of the commercial product.

The use of this invention, in this particular example, led to two distinctly different products of high value-added. One of them was identical to the currently commercially available product manufactured by conventional technology, in terms of colour characteristics, fluidity, handling characteristics, dispersion and solubility characteristics. This invention, however, provided this extract in a much reduced time, hence at reduced processing costs. Furthermore, the use of this invention also led to the production of a second, distinct, extract that possessed significantly different organoleptic properties and dispersion and solubility properties that made it a valuable product in other food applications requiring enhanced water solubility properties.

In summary, the use of this invention, as typified by this example, which is not exhaustive nor limitative, led to the production of a range of products from the same technology in a fraction of the time required by other methods. Thus, this invention allows for the design of extracts with specific physical and/or chemical properties. On an analytical-scale basis, it will be apparent to those skilled in the art that the use of this invention will enhance analytical protocols by providing a more tailored and more specific extraction scheme. This sample preparation step also requires a fraction of the time necessary for other methods, uses less solvent, bench space, energy and is less labour-intensive than, e.g., soxhlet, or other conventional extraction processes. All of these parameters makes it a technology of choice for most sample preparation aiming at the analysis of the material being subjected to the invention. This example also serves to show that the use of this invention was critical in obtaining, at the analytical-scale, a better extract, containing less fats, as evidenced by the much improved resolution that was recorded for the gas chromatographic traces of the MAP extracts, versus the commercial product. The ability to differentially heat the matrix, over the surrounding medium, even only for a fraction of the time, being the main reason for this phenomenon, hence the use the sequential irradiation when using ethanol as the extractant for MAP-9-2 to minimize temperature increase in the ethanol medium.

EXAMPLE 10

In their original form, black pepper kernels, a highly praised aromatic and flavouring substance with numerous food applications, is made of well-defined microstructural characteristics. Black pepper kernels are usually mill-ground (0.1 to 0.5 cm) just prior to their use in domestic applications. The same processing must be done prior to extraction when it is intended to perform an extraction with the aim of analyzing for the contents of the material. This coarse grinding process does not destroy entirely the microstructure of the material and the resulting powdery material still possesses a well-defined residual microstructure. This example is descriptive, but not exhaustive nor limitative, of a "just-in-time" sample preparation step preceding an extraction scheme that is applicable from the analytical-scale to the industrial scale. A sample of food-quality black pepper kernels (20 G) was ground with a mortar and pestle and subsequently placed in an erlenmeyer and immersed with hexane (30 mL). The mixture was subjected to microwave irradiation operating at 2450 MHz and at a nominal power of 625 Watts for 30 seconds. The resulting solution was filtered over anhydrous sodium sulphate and the remaining vegetable biomass was rinsed with hexane (3×20 mL). The extract was evaporated in vacuo and subsequently analyzed by gas chromatography-mass spectrometry as well as for its organoleptic properties. This extract is hereafter referred to as MAP-10.

A sample of an extract certified to have been produced from the same lot of vegetable material was obtained from the same manufacturer. For comparison purposes, it was also subjected to similar analyses.

All analyses methods along with the standard reference extraction method will be well-known to those skilled in the art.

The mass spectrometric analyses of both extracts provided evidence that they were identical in terms of the nature of the contents although the extract MAP-10 was characterized by a better gas chromatographic resolution. This is related to the lower contents in fats resulting from the short exposure time to solvent, combined with the judicious differential heating process applied to the mixture. This holds true for longer exposure time, at least at the beginning of the irradiation, although the extracts so obtained will then contain more fats as a result of the enhanced heating applied to the system.

The commercial product is a very thick, very viscous, dark blackish-green liquid with a distinctive pungent black pepper aroma with high terpene notes. The extract MAP was a greenish-brown fluid liquid with low viscosity. It possessed light aroma characteristic of black pepper.

When applied onto salt plates (2% extract, 3% polysorbate 80, and 95% sodium chloride) the organoleptic properties were determined as follows. The commercial product presented an oily aspect and was characterized by a light yellowish-green hue; it possessed a strong and distinctive black pepper aroma with high terpene notes, as well as a full, characteristic hot, pungent and piny black pepper flavour. The extract MAP-10 was also oily in aspect but presenting a brownish-yellow colour. Its aroma was very weak, although characteristic of black pepper. Its flavour, on the other hand, was very pungent and very hot and less characteristic of black pepper.

The samples were diluted at 1% in 99% water and further tested. The commercial product led to a slightly cloudy solution with a weak green hue that possessed a full, pungent, piny, black pepper flavour with the heat sensation developing mostly on the tongue. The extract MAP-10 also led to a slightly cloudy solution that possessed a light green hue. It was characterized by a flavour that was less full, much more pungent and less piny. The heat sensation was much more pronounced and developed in the back of the mouth, at the height of the throat.

For further comparison purposes, the MAP-10 extract was also diluted to 0.75% in 99.25% water (i.e. a reduction of 25% in the use of the extract) and further tested. The pungency and the heat sensation were then comparable to the commercial product, although the flavour was somewhat less full, with weaker terpene notes.

The solubility of the samples were determined in oil and in water. The commercial product was entirely insoluble in oil and hardly dispersed despite vigorous stirring. It was also insoluble in water as it sank as a result of its waxy properties. The extract MAP-10 was insoluble in oil but dispersed readily when stirred and fragmented into small particles when in contact with the oil. It was insoluble in water and spread readily across the surface without any stirring. It did not have waxy properties.

The use of this invention, in this particular example, led to an extract that was superior to the currently commercially available product manufactured by conventional technology, in terms of colour characteristics, fluidity, handling characteristics, pungency, heat sensation, dispersion and solubility characteristics. This invention, however, provided this extract in a much reduced time, hence at reduced processing costs. Furthermore, the use of this invention, in this particular example, provided commercial advantages such as producing an extract that is so pungent that it is possible to reduce by 25% the amount of extract used and to produce formulations making use of such an extract that exhibit similar properties. Thus a reduction in costs for the final product use. Similarly, at the analytical-scale, an enhanced resolution was obtained during the gas chromatographic analyses. This is the result of a cleaner extract (less fat and pigments) provided by this technology where differential heating was effected. This would represent reduced processing and analytical costs in a laboratory where a sample cleanup procedure can be avoided by the use of this invention when preparing the sample for analysis.

EXAMPLE 11

Animal tissues possess well-defined micro-structures that consist of vessels, cavities and other related structural entities. It is often required to extract, as selectively as possible, some animal tissues for specific chemical compounds such as nutrients, anti-nutrients, drugs, medicinal substances etc. The latter can be of a myriad of origins that include, but are not limited to plant, animal, human, processed products etc. It will be apparent to those skilled in the art that the following example, dealing with veterinary drug residues in a food safety analytical protocol, is only descriptive and not exhaustive nor limitative as the findings readily apply to a variety of other tissues (e.g. human tissues) in the course of a broad range of analytical methods (e.g. metabolites residues, forensic determinations).

3-Nitro-4-hydroxyphenylarsonic acid, hereafter called roxarsone after its commonly used name, is used as a general growth promoter for swine and poultry. The compound has been in use for numerous years at a time where little was known about the potential nutritional and toxicological effects on humans. There are official analytical protocols for the selective determination of roxarsone and for the non-selective, total arsenic contents, in feed and mixes, but there does not exist an official method for the direct determination of intact roxarsone in animal tissues. In fact, only a non-selective method is available and involves digestion of the animal tissues, hence destruction of the drug, prior to arsenic analysis by atomic absorption spectroscopy.

There is a general need for the extraction of intact drugs from animal tissues. For the purpose of this example, piglets were fed with various levels of roxarsone for 28 days at which time they were slaughtered and the liver, the kidneys and a portion of the hind quarters muscle were removed and processed in a meat grinder separately thus yielding three different types of tissues. A sample of ground tissues (1 g) was place in a screw-cap specimen container and spiked with an appropriate volume of a previously prepared standard solution of roxarsone so as to produce samples with tissue equivalent to 1, 2, 3, 4, and 6 parts per million (ppm) (the spiking procedures were actually performed by adding 100 µL of standard solutions prepared at 10, 20, 30, 40 and 60 µg/mL in water:isopropyl alcohol:trifluoroacetic acid in a ratio of 94:6:0,1 on a V:V:V basis). The spiked samples were left standing at room temperature for about 30 minutes prior to treatment (thus allowing for solvent evaporation and penetration of sample into the tissue).

For comparison purposes, the samples were treated by this invention, with ultrasound, or by homogenization. Absolute ethanol (25 mL) was spiked with glacial acetic acid (500 µL) to enhance the solubility of the product (an acid) into the ethanol. The spiked ethanol was added to the samples and the resulting mixtures were submitted to only one of the experimental treatments. The latter consisted of 9 seconds of microwave irradiation at 2450 MHz and at 750 watts followed by immediately decanting the supernatant for this invention, or to 90 seconds of ultrasound treatment, or to a full homogenization (i.e. destruction of structure) for 10 minutes. The subsequent treatment was identical for all samples, namely centrifugation of the sample (extract only for this invention) at 1380 G for 20 minutes at 273K. The clear supernatant was decanted and the resulting extract was reduced in vacuo and used for further high pressure liquid chromatography (HPLC) analysis. The HPLC analytical protocol will be evident to those skilled in the art and the following summary is provided only as a guideline. Mobile phase water:isopropyl alcohol:trifluoroacetic acid at 94:6:0,1 on a V:V:V basis; column PRP-1 with similar guard column; flow rate 1,0 mL/min; post-column treatment with 0,15 N sodium hydroxide delivered at 1,0 mL/min; detection on a UV-Vis detector at 410 nm.

The analytical results from these extractions exhibited the same trends. For example purposes, the following table VII summarizes the data obtained from a series of 5 replicates from samples spiked at a 4 µg/g (ppm) level and where the acronym MAP (TM) is used to identify the results obtained from the use of this invention.

TABLE VII

| Tissues | Technique | % Recovery |
| --- | --- | --- |
| Liver | Homogenization | 50,6 ± 13% |
|  | Ultrasound | 60,4 ± 12% |
|  | MAP-11 | 82,4 ± 3,0% |
| Kidney | Homogenization | 37,6 ± 3,7% |
|  | Ultrasound | 42,7 ± 11% |
|  | MAP-11 | 74,7 ± 2,4% |
| Muscle | Homogenization | 40,5 ± 19% |
|  | Ultrasound | 44,3 ± 10% |
|  | MAP-11 | 80,8 ± 2,2% |

It will be evident to those skilled in the art that no attempts were made to optimize the quantity of solvent being used and that the results would have been even better in terms of % recoveries if the centrifugation step, for this invention, would have been effected as per for the other methods, i.e. with the tissues. For the purpose of this example the extract was decanted right away as the example was intended to show unequivocally the value of this invention and to avoid any contribution due to passive dissolution and extraction into the medium as well as the contribution of the actual centrifugation (an extraction process in its own right). Furthermore, losses were also incurred in two steps for this invention (two decanting steps) instead of one and the extra step was more pronounced as the solvent was not well expressed out the residual biomass as it is the case for the centrifuged material. Despite these experimental conditions, the use of this invention led to a much higher recovery, with a greater reproducibility than current technologies. The extracts obtained by this invention were also cleaner as evidenced from the corresponding HPLC traces where less interferences were recorded. An official method would require sample cleanup procedures for the conventional methods; this invention, however, would not be subject to this requirement if used along with this analytical protocol. These advantages were obtained in a shorter time, hence at reduced costs. It will also be evident to those skilled in the art that the optimization of the extraction conditions in terms of volume required combined to multiple sample extraction and to a reduced number of experimental steps to be performed would bring about supplementary monetary benefits.

EXAMPLE 12

It will be evident to those skilled in the art that the present invention is not limited to biological materials that possess a uniformly well-defined structure. Biological material is used in its broad context, after the Second College Edition of The American Heritage Dictionary (1982) (biological: Of, pertaining to, caused by, or affecting life or living organisms). For example, a preferred application of the invention is related to the extraction from soils of numerous chemical components, of natural, e.g. humic acid and petrochemicals, or non-natural origins, e.g. contaminants such as, for example, pesticides. Soils are the result of the decomposition of living matters and contribute significantly to the existence of numerous living organisms in addition to playing an important role in the life of the plant kingdom. (Soil: the top layer of the earth's surface, suitable for the growth of plant life.) As weathering processes take place the soils change their nature but maintain to a significant extent well-defined structural characteristics that make them amenable to the use of this invention.

Soils are an example of biological or organic-containing materials that are characterized by non-uniform well-defined structure. Such structure consists of capillaries and physical binding sites that are related in broad terms to vessels and cavities (such as e.g. cells and glands found in other types of biological material such as e.g. leaf tissues from a plant). The mode of action of this embodiment of the invention is similar to that described above for the mint leaves example, but is more dependent upon the differential heating brought about by the microwave irradiation. Capillaries are quite often very resistant to physical stress and, as the name implies are open-ended vessels. It is through these open ends that several materials, e.g. pesticides, diffuse into the capillaries and often bind, almost irreversibly, to the surface of the capillaries. When using this invention the same phenomenon of local heating takes place, but given the open-ended nature of the capillaries, the contents, when submitted to the ensuing temperature and pressure increases, are expelled via the extremities of the capillaries. In some cases, some capillaries being weaker than others, the actual structural characteristics of the capillaries will be modified as the result of the explosion, at the microstructural levels, of some of the surfaces making up the capillaries. Similar phenomena occur with respect to the microstructures of the physical cavities that serve as binding sites to the various chemicals that find their way into the soils. It will be evident to those skilled in the art that such chemicals can come from natural sources, e.g. leaf falling from tree, or from non-natural sources, e.g. pesticides spraying, and that, consequently, the examples provided herein are not exhaustive nor limitative of the use of this invention for the extraction of a variety of chemical substances from biological and organic matter containing materials.

There is a need not only to remove chemicals from soils that are dispersed throughout the soils, but also to extract the so-called bound-residues, i.e. materials that until the advent of this invention were often considered as "irreversibly" bound to the soil matter. To demonstrate the effectiveness of this invention for work involving soils, a series of well-characterized soils (standard soils with well-characterized physical properties such as water contents, electric conductivity, pH, %-carbon, %-organic carbon, %-nitrogen, %-sand, %-clay, cation-exchange capacity) were used as is or wetted with known quantities of water and immersed in the presence of an extractant, namely hexane, and submitted to this invention and the resulting temperature increase brought about in the extractant was measured. The microwave irradiation (625 Watts operating at 2450 MHz) was applied for 30 seconds on individual samples consisting of 2 grams of soil, to which was added 0 or 1 mL of deionized water, that was covered with 10 mL of hexane. The resulting increase in temperature was recorded right at the end of the irradiation and measurements were taken at timed intervals for 5 minutes thereafter. For comparison purposes and to monitor the effect of the nature of the soil on the efficiency of this invention, 2 dummy samples consisting of 10 mL of hexane only and of 1 mL of water immersed in 10 mL of hexane were also subjected to similar treatment. All temperature measurements, made with an appropriate thermocouple, along with other physical properties measurement methods will be well-known to those skilled in the art. The following 2 tables summarize the properties of the soils and the results.

TABLE VIII

Physical properties of various soils subjected to the use of this invention

| Physical property | Soil 5 | Soil 7 | Soil 8 |
| --- | --- | --- | --- |
| pH in water (for a 1:1 ratio, w:w) | 6.6 | 7.3 | 7.6 |
| %-carbon | 2.96 | 4.43 | 1.46 |
| %-organic carbon | 2.90 | 4.24 | 1.32 |
| %-nitrogen | 0.26 | 0.35 | 0.14 |
| %-sand | 28.7 | 32.9 | 45.3 |
| %-clay | 26.2 | 29.1 | 28.1 |
| Cation-exchange capacity (meq/100 g) | 24.2 | 33.4 | 21.7 |
| Conductivity (mS/cm) | 0.07–0.48 | 0.23–0.71 | 0.29–2.07 |

TABLE IX

Temperature increase with time after 30 seconds of microwave irradiation

| Time (s) water added (mL) | Soil 5 | | Soil 7 | | Soil 8 | | Water | Hexane |
| --- | --- | --- | --- | --- | --- | --- | --- | --- |
| | 0 | 1 | 0 | 1 | 0 | 1 | | |
| 10 | 1.0 | 4.9 | 1.0 | 4.9 | 1.0 | 6.0 | 10.7 | 1.0 |
| 20 | 1.3 | 7.5 | 1.3 | 7.6 | 1.4 | 9.2 | 15.6 | 1.3 |
| 30 | 1.5 | 8.6 | 1.5 | 8.7 | 1.6 | 11.2 | 17.4 | 1.5 |
| 40 | 1.6 | 9.5 | 1.7 | 9.6 | 1.8 | 11.8 | 18.3 | 1.6 |
| 50 | 1.7 | 10.3 | 1.8 | 10.5 | 2.0 | 12.2 | 19.0 | 1.7 |
| 60 | 1.8 | 11.0 | 1.9 | 11.3 | 2.1 | 12.5 | 19.6 | 1.7 |

The use of the teachings of this invention, namely rehydration in this example, brought about a very selective differential heating of the matrix. The results provided in Table IX clearly indicate that the extractant remains cold when no matrix is present. They also demonstrate unequivocally that the addition of water enhances the differential heating of the biological material as a non-negligible portion of the heat generated by the water is dissipated to the biological material. A significant attribute of the invention lies with the fact that most soils, when rehydrated, can be regarded as being similar, in terms of behaviour, despite the very wide variation that they exhibit in terms of physical properties. This is a valuable attribute when compared to conventional solvent-extraction where the water contents of the soils affect the efficiency of the extraction to a great extent. The moisture content in soils may vary from about 20 to about 90% by weight for the method.

It will be evident to those skilled in the art that the amount of water to be added will be somewhat dependent on the ability the soil will have to absorb, and to a certain extent, to bind, the water. There is, however, the possibility to exceed such a threshold value by adding an excess of water. Furthermore, if even extra differential heating is required or desirable, it is possible for the user of the present invention to add saline solutions instead of water, or to add other highly microwave-absorbing species with large loss factors, as described earlier in our disclosure. The nature of these substances have to be acceptable and compatible with the following steps, e.g. analysis, ingestion, etc., and the choice of such substances will be evident to those skilled in the art.

It will also be evident that the use of an extractant devoid of microwave-absorbing characteristics will favour the differential heating over the use of a less-transparent extractant. Hence, the choice of the extractant will be guided by the desired amount of differential heating.

It will be evident that from the above teachings and examples that the present invention is applicable to various biological materials such as biomass including cellulosic materials. For example, another preferred application of the invention is related to the extraction, from particulates that were deposited onto cellulose, of numerous chemical components, of natural, e.g. volatile organics, or non-natural origins, e.g. contaminants such as, for example, PAHs (polyaromatic hydrocarbons). Cellulose biomass from the metabolism of plant materials is processed and used in numerous ways, including the manufacture of filter media that are used to collect particulates during, e.g. air or liquid filtration. As filtration takes place, the relatively well-defined micro structural characteristics of cellulose remain unchanged and make it amenable to the use of this invention.

As a further example, the techniques of this invention can be used to accelerate the extraction of components of particulates deposited onto a filtering device (e.g. made of cellulose). The mode of action is similar to that described above for soil. Cellulose by itself can absorb microwaves preferentially to, e.g. hexane. However, it has been found to be advantageous in the use of this invention with cellulose to add a dispersed component into the cellulose matrix prior to filtration, so as to further increase the efficiency of the differential heating that will result from the subsequent exposure to microwave radiation.

It has been found that the impregnation of saline solution, in appropriate concentration, prior to the use of the filtering device is a preferred aspect of this invention when extracting organic compounds, e.g. PAHs from particulates deposited onto the filtering device. For example, the sequence consisting of: impregnating the cellulose filtering medium with a saline solution, e.g. aqueous KCl or NaCl solution; drying the filtering medium; using the filtering medium as if untreated; adding water just prior to microwave irradiation so as to rehydrate the ionic matter; and using this invention gives rise to a more significant temperature differential than if used without the dispersion of highly-absorbing species.

The mode of action is simple, the impregnation of an aqueous solution onto the filtering device allows the dispersion of ionic substances into the filtering device, when subjected to drying only the water is removed leaving behind the ionic matter in non-mobile state. The presence of such dispersed material does not affect the filtering behaviour and characteristics of the medium with respect to, e.g., air filtration. Once filtration is achieved it is possible to free the ionic matter by rehydrating it by adding water to the filtration device prior to subjecting it to this invention, namely, microwave irradiation when immersed into a relatively transparent solvent, e.g. hexane or hexane-acetone mixture for PAHs. The differential heating so produced is then transmitted to the deposited particulates by diffusion and effects the release of the substances that were absorbed onto the particulates.

EXAMPLE 13

Prior to use in filtration, a cellulose filtering medium was impregnated with a saline (KCl) solution in the amount of 2 ml. of an aqueous 10% KCl solution per 10 g of filter medium and the medium dried. After the treated filter medium was used in air filtration, 2 ml of water was added to the medium, to rehydrate the deposited salt. The remoistened filter medium having dispersed saline solution and filtered matter therein, was subdivided into pieces about 1 $cm^2$ in size and the pieces immersed in hexane. This mixture was exposed to microwave as in Example 12 and the temperature differential between the filter medium and the surrounding hexane observed. The hexane extractant subsequently was analyzed for organics released from filtered particulates.

A more significant temperature differential was observed than if no ionic, highly microwave absorbing species had been used. The release of organic components into the hexane was more rapid and more complete compared to the absence of dispersed salt ions.

The concentration of saline solutions used may range from about 0.001M up to saturation and the amount of salt dispersed may range from about 0.001% to about 20% by wt of the material to be treated.

This way of using this invention is a preferred example when partially transparent solvents are used. In fact, a saline solution such as NaCl at 0.5M provides enough heat to effect the desired differential heating over practically any organic solvent. Hence, the use of mixtures such as hexane-acetone which are less effective in this invention than hexane alone can be improved by using this technique of the invention. Such methods can be applied to gas-phase and liquid-phase filtration processes and the component to be dispersed will be chosen, preferentially, from highly absorbing species that do not interfere with the subsequent use of the extract, be it for analytical, human or animal consumption, or any other purposes. Consequently, the examples provided herein are not exhaustive nor limitative of the use of this invention for the extraction of a variety of chemical substances from biomass of many types.

DETAILED DESCRIPTION OF THE PREFERRED APPARATUS EMBODIMENTS

Figure 1:
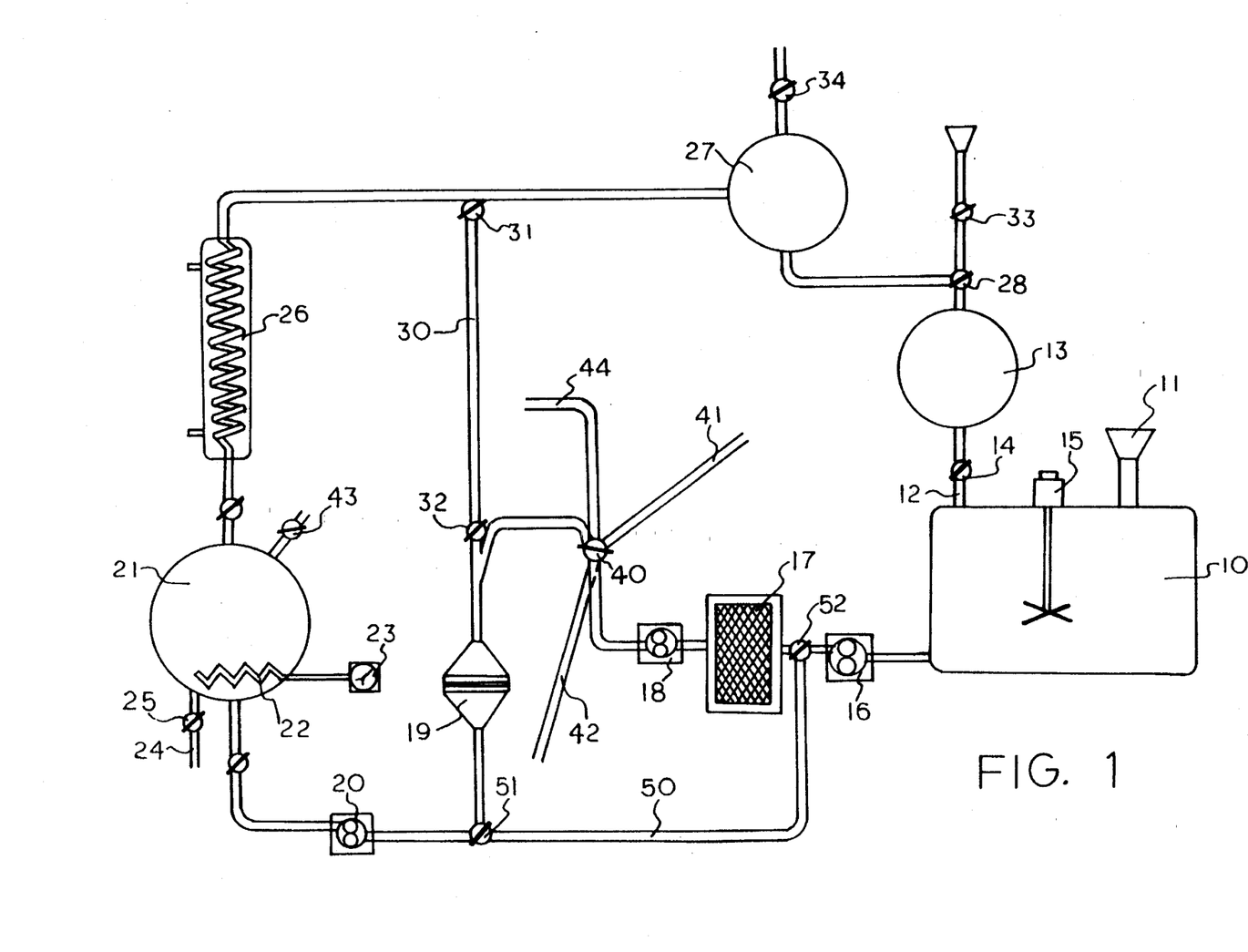
FIG. 1 is a diagrammatic representation of the apparatus of the present invention.

Referring now to FIG. 1, shown is the apparatus of the present invention having a reservoir or tank 10 with an inlet 11 for the biological material and an inlet 12 for the solvent previously discussed, which may be stored in solvent reservoir 13. Feeding the solvent into the tank 10 is controlled by valve 14. The mixture of solvent and biological material is stirred by a stirrer 15. A pump 16 feeds mixed solvent and plant material through a microwave applicator 17, (consisting of one or several sources) with a typical power rating of about 200 to about 10,000 Watts and a typical operating frequency of between 2,000 to about 30,000 MHz. Further, pump 18 feeds the treated material and solvent to a filtering apparatus 19. Also, a microwave source could be positioned within the supply tubing to enclose it within the feed material tube. The microwaves act directly on the cellular material to disrupt the same subsequently releasing the oils or other substances into the extractant for cooling thereby.

A plurality of filters used with or without desiccants may be provided in the filtering apparatus, acting in parallel. This enables filtered residual biological solids to be removed periodically from individual filters, without shutting down the apparatus completely.

From the filtering apparatus 19, the filtered solvent and oils therein are pumped, by pump 20, to a separator 21 or recycled to the microwave applicator 17 via valves 51 and 52 and tube 50. Separator 21 is heated, as by external heater 22, controlled by a temperature controller 23, to evaporate the solvent. The remaining substance or substances in the separator 21 is drawn off periodically at outlet 24 controlled by valve 25.

Evaporated solvent is passed through a condenser 26, and condensed solvent is fed back into a main reservoir 27 where it is then fed to the solvent reservoir 13, controlled by valve 28. In a modification, the condensed solvent could be fed directly to the solvent reservoir 13.

Some of the condensed solvent can be diverted through the filter 19 to increase the extraction in the filter. This is provided by pipe 30, controlled by valves 31 and 32. Various relief valves are provided, as at 33 and 34, for opening the apparatus to atmospheric pressure.

As described previously herein, the apparatus is for obtaining volatile oils and other substances by the use of microwaves to disrupt the glandular cells containing such oils. The apparatus can be combined with other conventional forms of apparatus. For example, a distribution valve 40 is provided between the microwave applicator 17 and the filter apparatus 19. From the valve, depending upon its setting, the mixed biological material and solvent can be fed to the filtering apparatus 19, as described above, or fed via a connection 41 to a conventional steam distillation plant. With such an application, the solvent is water and the mixed biological material and water can be treated in the microwave applicator, the water being heated. Alternatively, the water can be heated by the microwave applicator 17 until it reaches the vapour phase, under pressure, and is allowed to condense via connection 41, through the biological material that would be placed into the steam distillation reservoir (hydrodistillation and hydrodiffusion).

In another alternative, valve 40 can be set to permit flow through a connection 42 to a solids/liquid extraction plant. The mixed plant material and solvent may or may not be treated in the microwave applicator for the duration of the initial fill-up reflux sequence. The reflux of this operation could be returned directly to pump 16 for subsequent operations.

A particularly preferred form of the apparatus described above is utilized in conjunction with a supercritical fluid extraction process wherein the microwave applicator utilizes a system of tubing, such as glass, quartz or the like connected to or enclosed within an outer tubing of metal such as steel and in which the microwave apparatus uses an axially positioned microwave generating means within the tube and through which the material to be irradiated flows. In this way, a continuous process with its advantages can be utilized. Still further, other arrangements may be employed where the microwave generating means may be positioned surrounding a microwave transparent tube or conduit and in which the generating means is shielded by suitable material e.g. metal. In such a case, the transparent conduit material can be Teflon (TM) or glass.

For improved operation, it may be desirable to operate the system under vacuum conditions. More particularly, solvent removal by evaporation is greatly facilitated by reducing the pressure while maintaining a relatively low temperature. Connections at 43 and 44 provide for connection to a vacuum source.

The apparatus provides for increased extraction of certain essences and other substances which must be removed, or are preferably removed, without the application of heat, as by heating with a solvent.

Although specific embodiments of the present invention have been described above, it is not limited thereto and it will be apparent to those skilled in the art that numerous modifications form part of the present invention insofar as they do not depart from the spirit, nature and scope for the claimed and described invention.

I claim:

1. A method of treating materials comprising organic matter to disrupt the microstructure thereof, said materials having therein a substance which is difficult to access for extraction, which comprises:

(a) providing a source material to be treated in which the material includes organic matter and has at least one component which absorbs microwave radiation;

(b) mixing the material with a solvent which is relatively transparent, compared to the material to be treated, to microwave radiation; and (c) exposing the resulting mixture to microwave radiation until access to said substance by the solvent is facilitated.

2. The method of claim 1 wherein the concentration of said component in step (a) is adjusted before step (c) to increase the absorption of microwave radiation in step (c).

3. The method of claim 1 wherein the component is moisture and the moisture content is selected within about 20 to about 90% by weight.

4. The method of claim 1 wherein the organic matter is selected from the group consisting of seeds, cellulosic materials, and animal tissues.

5. The method of claim 1 wherein the materials treated are selected from the group consisting of soils, corals, low grade coals, and peats.

6. The method of claim 1 wherein said component in (a) is selected from the group consisting of water, bound water or salt solutions.

7. The method of claim 1 wherein the exposure to microwave in step (c) is carried out in a sequence of short intervals.

8. The method as defined in claim 1, comprising the steps of:

immersing a source material comprising organic matter and having a microstructure containing substances difficult to extract, in a non-aqueous organic extractant, said source material having a moisture content sufficient to cause disruption in said microstructure under microwave treatment;

exposing said source material to a microwave energy source to elevate the temperature of said material to a degree sufficient to disrupt said microstructure and release said substances from the material into said organic extractant;

recovering said substances released into said organic extractant.

9. The method of claim 1 wherein a highly microwave absorbing substance, relative to the solvent, is dispersed into the material to be treated before step (b).

10. The method of claim 9 wherein the solvent in step (b) is selected to have enhanced solvent action on substances to be extracted while sacrificing a portion of transparency to the microwave radiation.

11. The method of claim 1, wherein said source material is a soil material.

12. The method of claim 11, wherein the organic matter is a chemical.

13. The method of claim 11, wherein moisture is added to the soil prior to the soil being mixed with said solvent.

14. The method of claim 1, wherein said source material is a biomass material.

15. The method of claim 14, wherein the biomass material is a cellulose biomass.

16. The method of claim 1, wherein the source material is devoid of moisture, and which includes the further step of rehydrating or resolvating the source material with a substance having a greater net dipole moment than said source material, prior to mixing with said solvent.

17. The method of claim 1, wherein the solvent comprises a mixture of at least two extractants.

18. The method of claim 7, wherein the microwave frequency is chosen to selectively heat said at least one component.

19. A method of claim 1, wherein the microwave radiation is applied in a plurality of sequential treatments.

20. The method of claim 7, wherein said component of said source material is water and the microwave frequency is selected to enhance the extraction relative to said source material.

* * * * *